United States Patent [19]

Gotoh et al.

[11] Patent Number: 5,041,647
[45] Date of Patent: Aug. 20, 1991

[54] PROCESS FOR PRODUCING TRIFLUOROACETIC ACID AND TRIFLUOROACETYL CHLORIDE

[75] Inventors: Isao Gotoh, Yokohama; Hajime Yoneda, Ichihara; Seisaku Kumai, Tokyo; Tohru Ueno, Yokohama, all of Japan

[73] Assignee: Asahi Glass Co., Ltd., Tokyo, Japan

[21] Appl. No.: 930,056

[22] Filed: Nov. 12, 1986

Related U.S. Application Data

[63] Continuation of Ser. No. 730,552, May 6, 1985, abandoned.

[30] Foreign Application Priority Data

May 15, 1984 [JP] Japan .................................. 59-95537
May 15, 1984 [JP] Japan .................................. 59-95538
May 15, 1984 [JP] Japan .................................. 59-95539

[51] Int. Cl.$^5$ ...................... C07C 51/04; C07C 51/21; C07C 53/18
[52] U.S. Cl. .................................. 562/605; 562/541; 562/859
[58] Field of Search .............................. 562/541, 605

[56] References Cited

FOREIGN PATENT DOCUMENTS 0061594 10/1982 European Pat. Off. .
58-159440 9/1983 Japan .................................. 562/541

OTHER PUBLICATIONS

Asahi Glass Co., Chemical Abstracts, 100:85270u, (1984).
Levenspiel; Octave, The Chemical Reactor Minibook, OSU Book Stores, Inc., Corvallis, Oreg., 1979, 4.1 and 61.4.

Primary Examiner—Vivian Garner
Attorney, Agent, or Firm—Oblon, Spivak, McClelland, Maier & Neustadt

[57] ABSTRACT

A process for producing trifluoroacetic acid and trifluoroacetyl chloride from 1,1-dichloro-2,2,2-trifluoroethane, oxygen and water as starting materials, characterized in that the starting materials are reacted in a vapor phase in a reactor of perfect mixing type to avoid local heating, under a condition not to liquefy the starting materials and reaction products, while continuously supplying the starting materials and continuously withdrawing the reaction products, so as to obtain a reaction mixture comprising trifluoroacetyl chloride as the main product and trifluoroacetic acid as an accompanying product.

1 Claim, 1 Drawing Sheet

PROCESS FOR PRODUCING TRIFLUOROACETIC ACID AND TRIFLUOROACETYL CHLORIDE

This application is a continuation of application Ser. No. 730,552, filed May 6, 1985, now abandoned.

The present invention relates to a process for producing trifluoroacetic acid (hereinafter referred to simply as "TFA") and trifluoroacetyl chloride (hereinafter referred to simply as "TFAC") by reacting continuously 1,1-dichloro-2,2,2-trifluoroethane (hereinafter referred to simply as "R-123"), oxygen and water.

TFAC is useful as a starting material for the production of agricultural chemicals or medicines, and TFA is useful not only as a starting material for the production of agricultural chemicals or medicines, but also as a solvent for various reactions or as a catalyst for, e.g., esterification or condensation. Heretofore, for the production of these compounds, there have been known (1) a method for the production of TFA by electrolytically fluorinating acetyl fluoride (U.S. Pat. No. 4,022,824), (2) a method for the production of TFAC by reacting 1,1,1-trifluoro-2,2,2-trichloroethane with sulfur trioxide in the presence of a mercury salt (Japanese Unexamined Patent Publication No. 501649/1981), or (3) a method for the production of TFAC by reacting R-123 containing water in a small amount of less than 0.1% by weight with oxygen in the presence of active radiation. However, in the electrolytic fluorination, the separation of trifluoroacetyl fluoride as the intermediate product from hydrogen is costly. In the method wherein a mercury salt is employed, the reagent requires careful handling, and the method is accordingly industrially disadvantageous. In the method wherein active radiation is employed, the glass material of the radiation source will be devitrified by hydrofluoric acid produced in a small amount as a by-product, and can not be used for a long period of time. Thus, the conventional methods have some drawbacks.

The present applicants have previously proposed a process which overcomes the drawbacks of the conventional methods. Namely, the process comprises thermally oxidizing R-123 in the presence of water to obtain TFA and TFAC (Japanese Unexamined Patent Publication No. 159440/1983).

The present invention is an improvement over the process previously proposed by the applicants, whereby the conversion of R-123, the selectivity for TFA and TFAC and the reaction time have been improved.

Namely, the present invention provides a process for producing trifluoroacetic acid and trifluoroacetyl chloride from 1,1-dichloro-2,2,2-trifluoroethane, oxygen and water as starting materials, characterized in that the starting materials are reacted in a vapor phase in a reactor of perfect mixing type to avoid local heating, under a condition not to liquefy the starting materials and reaction products, while continuously supplying the starting materials and continuously withdrawing the reaction products, so as to obtain a reaction mixture comprising trifluoroacetyl chloride as the main product and trifluoroacetic acid as an accompanying product.

Now, the present invention will be described in detail with reference to the preferred embodiments.

In the accompanying drawings.

Figure 1:
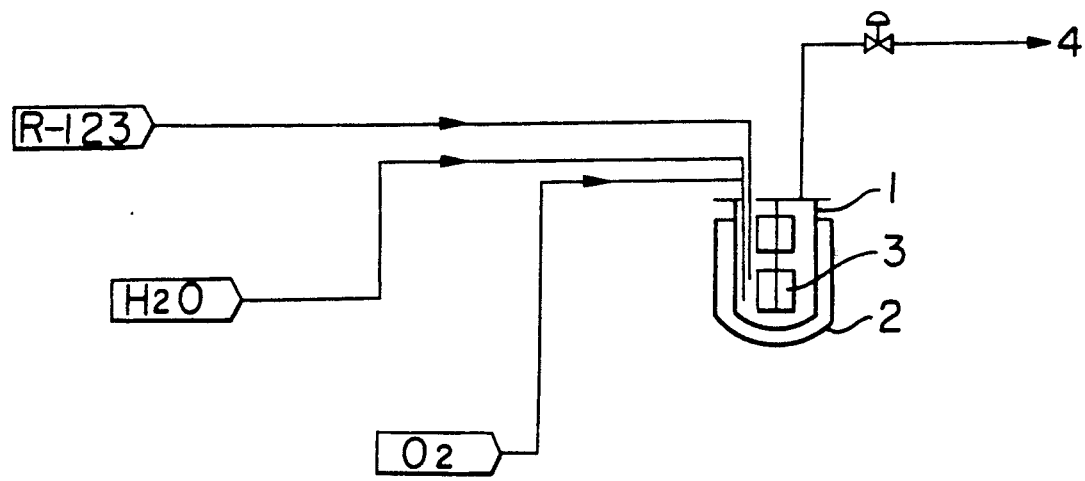
FIG. 1 is a flow sheet illustrating one embodiment of the process for the vapor phase reaction of R-123, oxygen and water.

The vapor phase reaction of R-123, oxygen and water is represented by the following formula:

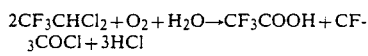

$$2CF_3CHCl_2 + O_2 + H_2O \rightarrow CF_3COOH + CF_3COCl + 3HCl$$

In the vapor phase oxidation reaction, the thermal decomposition reaction of R-123 and various accompanying side-reactions are likely to take place, thus leading to the formation of, e.g. HF. Further, during the preparation of R-123 as the starting material, it is likely that $CF_2ClCFHCl$ (R-123a) as an isomer of R-123, which is hardly separable from R-123, will be included in the starting material R-123. In an extreme case, R-123a will be included in an amount as high as 15% by weight. Consequently, hydrofluoric acid and hydrochloric acid are likely to form also by the oxidation reaction of R-123a, as follows:

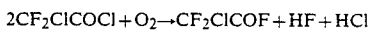

$$2CF_2ClCOCl + O_2 \rightarrow CF_2ClCOF + HF + HCl$$

On the other hand, in the case where TFA or TFAC is to be obtained by the oxidation of R-123 (which usually contains a small amount of the isomer R-123a as mentioned above), it is known that water functions catalytically, and, in the absence of water, the oxidation reaction of R-123 hardly takes place. However, the presence of water facilitates the corrosion of the apparatus by hydrofluoric acid or hydrochloric acid formed as a by-product as mentioned above. Particularly, hydrofluoric acid is highly corrosive even in the absence of water, whereby the glass covering the radiation source as disclosed in Japanese Examined Patent Publication No. 24416/1983 will not be durable for use for a long period of time. The same publication teaches that a glass or quartz light source will be damaged by hydrofluoric acid formed as a by-product during a liquid phase oxidation reaction of R-123. The present inventors have found that the same applies to the vapor phase oxidation reaction.

Thus, in the oxidation reaction of R-123 where water is used catalytically, it is impossible to use active radiation on an industrial scale in which glass material not durable to corrosion is required. Even in the vapor phase oxidation reaction where the presence of water is limited to a minimum amount, it is likely that water precipitates during the reaction process, whereby corrosion by hydrofluoric acid can not be avoided.

Whereas, in the process of the present invention, no active radiation is required, and the entire reactor may be made of, for instance, Hastelloy, whereby the danger of corrosion can be prevented, and an industrial operation for a long period of time is possible. Further, the presence of water is not required to be the minimum, since the danger of corrosion is minimum, and it is possible to improve the selectivity for TFA by adding water in an amount sufficient for the catalytic activity.

In the process of the present invention, the reaction is conducted under pressure at a high temperature of at least 200° C. and at an extremely high rate with the retention time in the reactor of within 10 minutes. Accordingly, in order to increase the conversion and improve the selectivity for TFA and TFAC by suppressing side-reactions, it is important to uniformly mix the reactants and maintain the temperature and concentrations at constant levels. The oxidation reaction of R-123 is an exothermic reaction wherein water is used as a catalyst. Accordingly, local superheating is likely to occur in the reactor, and side-reactions are likely to take place due to, e.g. the thermal decomposition, thus leading to a deterioration of the selectivity for TFA or TFAC. In order to avoid such local superheating, a stirrer may be provided in the reactor as shown at 3 in FIG. 1. In a vertical reactor as shown at 1 in FIG. 1, stirring vanes may be provided in one or a few vertically separated rows, and in a 50 liter reactor, for instance, stirring is conducted at a speed of at least 100 rpm, preferably at least 150 rpm, whereby the heat can effectively be dissipated. In order to maintain the entire reactor to a constant temperature level, a jacket may be provided as shown at 2 in FIG. 1 for the heat exchange with an external heat medium, or the heat exchange between the starting materials and the reaction products may also be employed. The reaction temperature in the vapor phase continuous reaction of the present invention is selected within a range of from 250 to 400° C., preferably from 260 to 320° C. when a reaction pressure of from about 25 to about 35 kg/cm² is employed. If the temperature is lower than the above range, the reaction rate tends to decrease, or in an extreme case, no reaction takes place. On the other hand, if the temperature exceeds the above range, side-reactions such as thermal decomposition reactions are likely to take place, such being undesirable.

According to the process of the present invention, a reactor of perfect mixing type is employed, whereby the temperature and concentration can be maintained at a constant level by the perfect mixing. For this purpose, in addition to the above-mentioned stirring and heat exchange operations, it is preferred to employ a method wherein the starting materials for the reaction are supplied to a lower portion of a vertical reactor as shown at 1 in FIG. 1, and the reaction product is withdrawn from an upper portion. Further, as shown in FIG. 1, R-123 is preferably supplied at a position higher than the position for the supply of oxygen or water, whereby R-123 can more uniformly be mixed with oxygen and water, and thus the conversion of R-123 and the selectivity will be improved. If the mixing of the starting materials is incomplete, unreacted R-123 will accumulate, whereby there is a danger of explosion due to an instantaneous oxidation reaction of the large amount of accumulated R-123. Also in this respect, it is important to conduct the mixing operation thoroughly. In order not to permit R-123 to remain unreacted, the amount of the oxygen relative to R-123 should preferably be at least the theoretical amount, and it should preferably be not higher than two mols per mol of R-123 to avoid explosion. Thus, the amount of oxygen supplied is selected within a range of from 0.5 to 2 mols, preferably from 1 to 2 mols, per mol of R-123.

The present inventors have found that if the starting materials or the reaction products are liquefied even in a very small amount in the reactor, liquid drops will deposit on the wall of the reactor, and corrosive substances such as HCl or HF formed as by-products will be dissolved in the liquid drops and will corrode the wall of the reactor, thus leading to undesirable results. A metal chloride forms as the result of the corrosion of the wall of the reactor, and the chloride acts as a negative catalyst to adversely affect or terminate the oxidation reaction, whereby there is a possible danger of explosion by instantaneous oxidation of unreacted R-123. R-123 as the starting material and HCl and HF formed as by-products are in a gaseous state at room temperature. Although the reaction temperature of the present invention is as high as about 300° C., the starting materials and reaction products are likely to be liquefied since the reaction pressure is as high as about 20 to about 40 kg/cm². Particularly, water which is liquid at room temperature, is susceptible to liquefaction in the reactor. Accordingly, an excess supply of water should be avoided. In the oxidation reaction of R-123, water is believed not only to act as catalyst but also to have a function to hydrolyze trifluoroacetyl chloride formed by the oxidation of R-123 and convert it to trifluoroacetic acid. Accordingly, the amount of water is preferably such that it is at least the minimum amount required for the catalyst and at most the amount where water does not liquefy and deposit on the wall of the reactor. The amount of the water is usually selected within a range of from 0.01 to 0.5 mol per mol of R-123. It is important not to permit the liquefaction of even a very small amount of the starting materials or the reaction products in the reactor, or to complete the oxidation reaction of the starting materials or disperse and withdraw the reaction products with the accompanying gas, prior to the deposition of the liquefied starting materials or reaction products onto the wall of the reactor. The liquefaction of the starting material gas can effectively be prevented by preheating it at a temperature of from 150° to 200° C. prior to the supply to the reactor. With respect to R-123 which is supplied in the largest amount and thus is most likely to liquefy, it is preferred to supply to the reactor at a position higher than the position for the supply of oxygen and water, as shown in FIG. 1, and in the vicinity of vanes of the stirrer to well disperse and complete the oxidation reaction. For the oxidation reaction of R-123 in a perfect mixing state as in the present invention where the temperature and concentration are constant, a vertical single-tower reactor for continuous operation may be employed in which the retention time of the gas in the reactor will be from 2 to 20 minutes.

The reaction mixture withdrawn from the reactor as shown at 4 in FIG. 1, is subjected to a separation operation by distillation to obtain desired TFA and TFAC. TFAC can readily be hydrolyzed to TFA. Accordingly, it is conceivable that in order to obtain only TFA in good yield, water may be added to the reaction mixture containing TFAC, in an excess amount required for the hydrolysis of TFAC to convert all TFAC to TFA. However, TFA forms an azeotropic mixture with water, and it is hardly separable by distillation. Thus, the above-mentioned operation in which unreacted water remains after the hydrolysis of TFAC, is not desirable.

In view of such a problem, the present inventors have conducted extensive researches for a process to efficiently convert TFAC to TFA, and have found the following interesting facts (1) and (2).

(1) Although it is difficult to remove water from water-containing TFA by distillation, it is possible to obtain TFA which contains no substantial water, by contacting TFAC to water-containing TFA to consume water for the hydrolysis of TFAC. When hydrolyzed, TFAC is readily converted to TFA, and remaining TFAC can readily be separated from TFA by the difference in the boiling points.

(2) In the above (1), water-containing TFA can readily be converted to TFA which contains no substantial water. Thus, the operation for the conversion of all TFAC to TFA by reacting TFAC with an excess amount of water, i.e. the operation for the formation of water-containing TFA, is no longer disadvantageous.

On the basis of these discoveries, the present inventors have found a process whereby only TFA can be obtained in good yield.

Namely, present invention also provides a process for producing trifluoroacetic acid, which comprises subjecting 1,1-dichloro-2,2,2-trifluoroethane, oxygen and a small amount of water to a vapor phase reaction to continuously obtain a reaction mixture comprising trifluoroacetyl chloride as the main product and trifluoroacetic acid as an accompanying product, reacting the reaction mixture with a large amount of water without subjecting it to a separation operation, whereby the trifluoroacetyl chloride is hydrolyzed and converted to trifluoroacetic acid, and withdrawing this trifluoroacetic acid together with the above-mentioned trifluoroacetic acid as the accompanying product.

Figure 2:
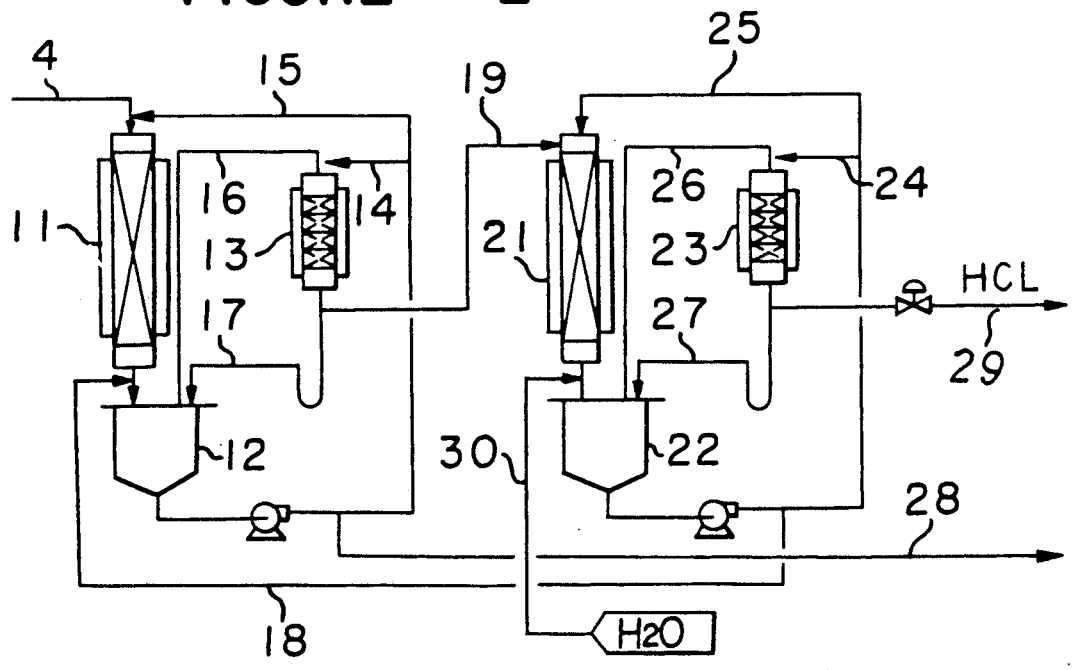
FIG. 2 is a flow sheet illustrating one embodiment of the hydrolytic process to convert TFAC to TFA.

The method for reacting the reaction mixture containing TFA and TFAC with a large amount of water without subjecting it to a separation operation, is preferably conducted by hydrolysis as shown in FIG. 2, which comprises a step of converting all TFAC to TFA with an excess amount of water, and a step of removing water from the resulting water-containing TFA by means of TFAC.

The reaction mixture supplied at 4 in FIG. 2 is composed mainly of TFA, TFAC, hydrochloric acid and unreacted oxygen. All operations in the flow sheet shown in FIG. 2 may be conducted at a normal temperature under atmospheric pressure. The above-mentioned hydrochloric acid and oxygen supplied from 10, will be sent in a gaseous state, via a first conversion-to-acetic acid tower 11, a first separation tank 12, a conduit 16, a first cooling tower 13, a conduit 19, a second conversion-to-acetic acid tower 21, a second separation tank 22, a conduit 26 and a second cooling tower 23 and discharged out of the system at 29, and thus they will be separated from desired TFA. Gaseous components at room temperature under atmospheric pressure in a TFAC-containing reaction mixture obtained by a method other than the oxidation reaction of R-123, are likewise discharged via the same route as above. The rate of the hydrolysis of TFAC is faster than the reaction rate of these gases with water, whereby there is no possibility that these gases to be removed, will remain by being liquefied or hydrolyzed.

TFAC to be hydrolyzed will pass on a gaseous state through the same route as the above-mentioned hydrochloric acid, but it is entirely hydrolyzed to TFA until it passes through the second cooling tower 23. Water for the hydrolysis is continuously supplied in an excess amount relative to TFAC accompanied by e.g. hydrochloric acid, and TFAC is hydrolyzed in the second separation tank 22, and converted to a TFA solution. The converted TFA solution and the remaining unreacted water are recycled via conduits 24 and 25. Those recycled via the conduit 24 is introduced into the second cooling tower 23, where a very small amount of TFAC which was not hydrolyzed in the second separation tank 22 and which is likely to be accompanied by, e.g. hydrochloric acid, is converted to TFA by water in the TFA solution, and then returned to the second separation tank 22 via a conduit 27. TFA is liquid at room temperature under atmospheric pressure, and therefore is not likely to rise through a conduit 26 as accompanied by, e.g. hydrochloric acid. However, if it is so accompanied, it will be liquefied in the second cooling tower 23 and returned to the second separation tank 22 via the conduit 27, whereby TFA will not be discharged out of the system as a loss. On the other hand, those recycled via the conduit 25, is introduced to the second conversion-to-acetic acid tower 21, subjected to hydrolysis and returned to the second separation tower. Such a recycling operation is continuously conducted, whereby a TFA solution containing from 1 to 10% by weight of water will be accumulated in the second separation tower 22. Having thus described the flow of the right hand side half of FIG. 2 including the second conversion-to-acetic acid tower 21, the second separation tank 22 and the second cooling tower 23, the entire flow will be referred to as step B.

The TFA solution containing a very small amount of water filled in the second separation tank 22, is intermittently transferred to the first separation tank 12. The TFA solution containing a very small amount of water in the first separation tank 12, is recycled via conduits 14 and 15. The solution recycled via the conduit 14 is introduced into the first cooling tower 13, where TFAC accompanied by, e.g. hydrochloric acid and not hydrolyzed in the first conversion-to-acetic acid tower 11 or the first separation tank 12, is converted to TFA by water in the TFA solution, and then returned to the first separation tank 12 via the conduit 17. Those recycled via the conduit 15 is introduced into the first conversion-to-acetic acid tower 11, subjected to the hydrolysis of TFAC in the reaction mixture 10, and then returned to the first separation tank 12. The first cooling tower has a role of liquefying TFA and returning it to the first separation tank 12 in the same manner as the second cooling tower in the step B. Such a recycling operation is continuously conducted, whereby a TFA solution having a water content of about 0.01% by weight will accumulate in the first separation tank 12. Having thus described the flow of the left hand side half of the FIG. 2 including the first conversion-to-acetic acid tower 11, the first separation tank 12 and the first cooling tower 13, the entire flow will be referred to as step A.

TFAC which was not hydrolyzed, is transferred to the second conversion-to-acetic acid tower 21 in the step B via the conduit 19, and eventually converted entirely to TFA by an excess amount of water introduced through a conduit 30. To the second conversion-to-acetic acid tower, not only such TFAC, but also TFAC supplied from 4 in FIG. 2 or the reaction mixture may be introduced. The TFA solution containing from about 1 to about 10% by weight of water accumulated in the second separation tank 22, may be supplied into the first separation tank 12 after the TFA solution in the first separation tank 12 having a water content of about 0.01% by weight has been withdrawn to the distillation step via the conduit 28. The amount of the supply of the TFA solution containing about 1 to about 10% by weight of water into the first separation tank 12, may be determined based on the amount of TFA from the hydrolysis of TFAC or the accumulated amount of TFA as the reaction product (hereinafter referred to as a freshly accumulated TFA amount). Namely, the amount of the supply is such that the first separation tank 12 is filled with a freshly accumulated TFA amount during a period of time in which the water content in the TFA solution in the first separation tank 12 changes, for instance, from 5% by weight to 0.01% by weight. Of course, it is not necessarily required to conduct the operation to such extent that the first separation tank is filled with the liquid 100%, and the withdrawal to the distillation system may be operated when about 80% of the tank has been filled.

The reaction mixture containing TFAC is continuously introduced into the first conversion-to-acetic acid tower. In the case where the water content in the TFA solution is large, the hydrolysis of TFAC is believed to take place primarily in the first conversion-to-acetic acid tower. As the water content decreases, the hydrolysis of TFAC tends to occur in the first separation tank. In the case where the temperature of the TFAC-containing reaction mixture supplied from 4 is high, the TFA solution is passed to the first conversion-to-acetic acid tower to conduct not only the hydrolysis but also the cooling operation. Otherwise, TFA in the first separation tank is likely to be vaporized by the supplied TFAC or its mixture and discharged from the step A.

The amount of water supplied from the conduit 30 is an amount required to certainly convert the entire amount of TFAC supplied from the step A to TFA. The position for the supply of water is not necessarily at the intermediate point between the second conversion-to-acetic acid tower and the second separation tank as shown in FIG. 1, and water may be supplied from the upper portion of the second conversion-to-acetic acid tower. In any case, it is preferred to convert all TFAC to TFA with a minimum supply of water. The water content in the TFA solution required not to let TFAC escape out of the system, is at least from 1 to 10% by weight. TFAC flowing from the conversion-to-acetic acid tower to the separation tank is preferably introduced deep into the TFA solution, while stirring the solution, in order to bring TFAC in good contact with water in the TFA solution. A packed tower is preferably employed as the conversion-to-acetic acid tower or the cooling tower, so that the contact of gas-liquid can adequately be conducted.

The above-mentioned step A means a step of obtaining TFA which contains no substantial water, and the step B means a step in which TFAC is reacted with an excess amount of water to hydrolyze all TFAC to TFA and thereby to obtain water-containing TFA. When the water-containing TFA obtained in the step B is used in the step A after the TFA containing no substantial water obtained in the step A was withdrawn, a water-removal operation will be conducted in this step A to obtain TFA containing no substantial water. However, it is also possible that the water-containing TFA obtained in the step B is used in this step B without transferring it to the step A, and the supply of the reaction mixture containing TFAC is switched from the step A to this step B to conduct the reaction, whereby the water-removal operation may be conducted in the step B. In this case, in the step B, the operation for the step A is conducted, and at the same time, in the step A after the withdrawal of TFA containing no substantial water, the operation of the step B is conducted. Namely, the step B described earlier is changed to the step A, whereby the water-containing TFA is, in effect, used in the step A without being transferred. Namely, the supply of the reaction mixture containing TFAC is switched from the first conversion-to-acetic acid tower 11 in FIG. 2 to the second conversion-to-acetic acid tower 21, whereby the earlier step A is used as a new step B, and the earlier step B is used as a new step A.

Now, the present invention will be described in further detail with reference to Examples. However, it should be understood that the present invention is by no means restricted by these specific Examples.

EXAMPLE 1

Into a 50 liter vertical reactor as shown at 1 in FIG. 1 equipped with a stirrer having vertically separated two sets of stirring vanes as shown at 3 in FIG. 1 and a jacket-type heat exchanger as shown at 2 in FIG. 1, R-123, water and oxygen were continuously supplied and reacted. The supply of R-123 was 103 mol/hr. R-123 was supplied to the reactor at a position lower than the position for the withdrawal of the reaction products and higher than the position for the supply of water and oxygen. These starting materials were supplied at a position in the vicinity of the lower stirring vanes. Further, R-123 and water were preheated. The reaction condition, the conversion of R-123 and the selectivity for TFA and TFAC are shown in Table 1. The conversion and selectivity were obtained by analyzing the reaction products by means of $^{19}$F-NMR and gas chromatography. The temperature difference in the reactor was determined as the difference in the temperature as between the center of the upper stirring vanes and the center of the lower stirring vanes.

TABLE 1

|  | Examples | | |
| --- | --- | --- | --- |
|  | 1 | 2 | 3 |
| Molar ratio of water/R-123 | 0.1 | 0.2 | 0.075 |
| Molar ratio of oxygen/R-123 | 1.0 | 1.0 | 1.0 |
| Preheating temperature (°C.) | 180 | 175 | 180 |
| Reaction temperature (°C.) | 300 | 260 | 300 |
| Reaction pressure (kg/cm$^2$) | 30 | 30 | 30 |
| Retention time (min.) | 8.4 | 7.2 | 8.4 |
| Temperature difference in the reactor (°C.) | 4 | 4 | 5 |
| Rotational speed of the stirring vanes (r.p.m.) | 150 | 120 | 160 |
| Liquid drops (mol/hr) | 0 | 0 | 0 |
| Conversion (%) | 95 | 91 | 95 |
| Selectivity for TFAC (%) | 68 | 65 | 68 |
| Selectivity for TFA (%) | 26 | 28 | 24 |

COMPARATIVE EXAMPLE 1

Into a Hastelloy C autoclave having an internal capacity of 200 cc and equipped with a mechanical stirring device, 10.5 g (0.067 mol) of R-123 and 0.12 g (0.0067 mol) of water were charged, and heated to 290° C., whereby the pressure was 15 kg/cm$^2$. Oxygen was supplied thereto and the pressure was raised to 30 kg/cm$^2$ and maintained at that level for 5 minutes. Then, the content was collected in a trap cooled by liquefied nitrogen. The trap was further immersed in a dry ice-ethanol bath to remove unreacted oxygen and the formed hydrochloric acid. Then, the reaction solution was analyzed by $^{19}$F-NMR and gas chromatography. As a result, it was found that the conversion of R-123 was 52%, the selectivity for TFA was 22%, and the selectivity for TFAC was 68%.

COMPARATIVE EXAMPLE 2

The reaction was conducted in the same manner as Comparative Example 1 except that the reaction time was extended to 8 minutes to increase the conversion of R-123. As the result, it was found that the conversion of R-123 was 53%, the selectivity for TFA was 20%, and the selectivity for TFAC was 64%. Namely, there was no substantial change in the conversion, but the selectivity was poorer.

EXAMPLE 2

Into a 50 liter vertical reactor equipped with a stirrer and a jacket-type heat exchanger, 103 mol/hr of $CF_3CHCl_2$, 10.3 mol/hr of $H_2O$ and 103 mol/hr of $O_2$ were continuously supplied, and the continuous vapor phase reaction of the present invention was conducted. The reaction temperature was 300° C., the pressure was 30 kg/cm², and the retention time was 8.4 minutes. The reaction products thereby obtained were analyzed by $^{19}F$-NMR and gas chromatography, whereby it was found that the conversion of $CF_3CHCl_2$ was 95%, the selectivity for $CF_3COOH$ was 26%, and the selectivity for $CF_3COCl$ was 68%. Then, the hydrolysis of the reaction products was conducted by two steps A and B. In the step A, 25.4 mol/hr of $CF_3COOH$ and 66.5 mol/hr of $CF_3COCl$ were continuously supplied in a recycling manner to 1197 mol of $CF_3COOH$ containing 5% by weight of $H_2O$, and water removal was conducted, whereby the water content became not higher than 0.01% by weight upon expiration of 24 hours. On the other hand, in the step B, 1596 mol of $H_2O$ was used for the hydrolysis of $CF_3COCl$ which was continuously supplied from the step A in a recycling manner, whereby 1197 mol of $CF_3COOH$ containing 5% by weight of $H_2O$ was obtained after expiration of 24 hours.

The amount of $CF_3COCl$ which was not hydrolyzed in the step A and which was supplied to the step B, was almost negligible until the water content in $CF_3COOH$ in the step A reached about 1% by weight, and rapidly increased as the water content approached 0.01% by weight.

EXAMPLE 3

The reaction and analysis were conducted in the same manner as in Example 2 except that the amount of supply of $H_2O$ was changed to 20.6 mol/hr, the reaction temperature was changed to 260° C., and the retention time was changed to 7.2 minutes. As the results, it was found that the conversion of $CF_3CHCl_2$ was 91%, the selectivity for $CF_3COOH$ was 28%, and the selectivity for $CF_3COCl$ was 65%. Then, the hydrolysis of the reaction products was conducted in two steps A and B. In the step A, 26.2 mol/hr of $CF_3COOH$ and 60.9 mol/hr of $CF_3COCl$ were supplied continuously in a recycling manner to 858 mol of $CF_3COOH$ containing 10% by weight of $H_2O$, and water removal was conducted, whereby the water content became not higher than 0.01% by weight upon expiration of 24 hours. On the other hand, in the step B, 1462 mol of $H_2O$ was used for the hydrolysis of $CF_3COCl$ supplied continuously in a recycling manner from the step A, whereby 858 mol of $CF_3COOH$ containing 10% by weight of $H_2O$ was obtained upon expiration of 24 hours. The amount of $CF_3COCl$ which was not hydrolyzed in the step A and which was supplied to the step B, was almost negligible until the water content in $CF_3COOH$ in the step A reached about 1% by weight and rapidly increased as the water content approached 0.01% by weight, in the same manner as in Example 2.

We claim:

1. A process for the continuous production of trifluoroacetic acid, which comprises:
   a) reacting 1,1-dichloro-2,2,2-trifluoroethane, oxygen and a small amount of water in the vapor phase to continuously obtain a reaction mixture comprising trifluoroacetyl chloride as the main product and trifluoroacetic acid as a by-product, and
   b) hydrolyzing the trifluoroacetyl chloride to trifluoroacetic acid in two steps A and B, said step A comprising contacting trifluoroacetyl chloride with water-containing trifluoroacetic acid to obtain trifluoroacetic acid containing substantially no water, and said step B comprising reacting trifluoroacetyl chloride with excess water to obtain water-containing trifluoroacetic acid, which is recycled for use in said step A; and wherein said reaction is conducted at a temperature within a range of from 250 to 400° C., and under a pressure within a range of from 25 to 35 kg/cm².

* * * * *